United States Patent
Suyama et al.

(10) Patent No.: US 10,925,557 B2
(45) Date of Patent: Feb. 23, 2021

(54) HIGH-ENERGY RAY DETECTOR AND TOMOGRAPHIC IMAGE ACQUISITION APPARATUS

(71) Applicant: HAMAMATSU PHOTONICS K.K., Hamamatsu (JP)

(72) Inventors: Motohiro Suyama, Hamamatsu (JP); Hideki Shimoi, Hamamatsu (JP); Ryosuke Ota, Hamamatsu (JP); Ryoko Yamada, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 0 days.

(21) Appl. No.: 16/543,728

(22) Filed: Aug. 19, 2019

(65) Prior Publication Data

US 2020/0093448 A1 Mar. 26, 2020

(30) Foreign Application Priority Data

Sep. 25, 2018 (JP) .............................. JP2018-178574

(51) Int. Cl.
- *A61B 6/00* (2006.01)
- *G01T 1/24* (2006.01)
- *A61B 6/03* (2006.01)

(52) U.S. Cl.
CPC ............ *A61B 6/4266* (2013.01); *A61B 6/032* (2013.01); *A61B 6/037* (2013.01); *A61B 6/481* (2013.01); *G01T 1/247* (2013.01); *G01T 1/249* (2013.01)

(58) Field of Classification Search
CPC ........ A61B 6/4266; A61B 6/032; A61B 6/037
See application file for complete search history.

(56) References Cited

U.S. PATENT DOCUMENTS

| | | | |
|---|---|---|---|
| 5,719,401 A | 2/1998 | Chaney et al. | |
| 6,492,657 B1* | 12/2002 | Burlefinger | H01J 31/48 250/207 |
| 8,604,440 B2 | 12/2013 | Frisch et al. | |
| 2008/0017805 A1* | 1/2008 | Takahashi | G01T 1/2935 250/385.1 |
| 2010/0001193 A1* | 1/2010 | Feller | G01T 1/202 250/366 |
| 2014/0124676 A1* | 5/2014 | Hedler | G01T 1/28 250/366 |

OTHER PUBLICATIONS

Tanaka, Y. T. et al., "Gamma-ray detection efficiency of the microchannel plate installed as an ion detector in the low energy particle instrument onboard the GEOTAIL satelite," Review of Scientific Instruments 78, 034501, 2007, pp. 1-4.

* cited by examiner

*Primary Examiner* — Hugh Maupin
(74) *Attorney, Agent, or Firm* — Faegre Drinker Biddle & Reath LLP

(57) ABSTRACT

A high-energy ray detector includes a detection unit in a vacuum container. The detection unit includes a first electron multiplier, a second electron multiplier, and an electron collector. Each of the first electron multiplier and the second electron multiplier has one or more MCPs each configured to emit electrons by interaction with an incident high-energy ray (γ-ray, X-ray (in particular hard X-ray), or neutron ray), and multiply and output the electrons. The electron collector is transmissive for the high-energy ray. The electron collector is configured to collect the electrons multiplied and output from each of the first electron multiplier and the second electron multiplier, and output an electric pulse signal.

8 Claims, 17 Drawing Sheets

HIGH-ENERGY RAY DETECTOR AND TOMOGRAPHIC IMAGE ACQUISITION APPARATUS

TECHNICAL FIELD

The present disclosure relates to a high-energy ray detector and a tomographic image acquisition apparatus.

BACKGROUND

As a detector for detecting an incident high-energy ray (for example, γ-ray), a detector described in Patent Document 1 is known. The detector described in this document has a configuration in which one detection unit is constituted by a Cherenkov radiator, a photoelectric conversion unit, a micro-channel plate (MCP), and an anode electrode, and a plurality of the detection units are arranged inside a vacuum container.

In each detection unit of the above detector, when Cherenkov light is generated in the radiator by interaction with an incident γ-ray, the Cherenkov light enters the photoelectric conversion unit, and electrons are emitted from the photoelectric conversion unit. The electrons emitted from the photoelectric conversion unit are multiplied by the MCP, and the electrons multiplied and output by the MCP are collected by the anode electrode, and an electric pulse signal is output from the anode electrode. According to the description in the document, the above detector can detect a time point when a photon of a γ-ray arrives, and accordingly, it is regarded that the detector can be used in a TOF-PET apparatus.

The detector for detecting γ-rays is used, for example, in a tomographic image acquisition apparatus. A positron emission tomography (PET) apparatus, which is a type of tomographic image acquisition apparatus, places an object into which a radio isotope (RI) source has been introduced in a measurement space, detects a photon pair of γ-rays generated along with electron-positron annihilation in the object using a coincidence method to collect coincidence information, and acquires a tomographic image of the object based on the collected coincidence information. A normal PET apparatus reconstructs a tomographic image of an object by repeatedly performing calculations according to a predetermined algorithm based on the collected coincidence information.

On the other hand, a time of flight (TOF)-PET apparatus, which is expected as a next-generation PET apparatus, can limit a coincidence line connecting two detectors to a length corresponding to a fluctuation of a difference in detection time point between the two detectors based on a difference in photon detection time point between the two detectors detecting a photon pair, for each electron-positron annihilation event in the object. The TOF-PET apparatus acquires a tomographic image of the object from a limited coincidence line obtained for each electron-positron annihilation event in the object.

Therefore, a signal to noise ratio (SNR) of the image is improved in the TOF-PET apparatus, as compared with the normal PET apparatus.

Patent Document 1: U.S. Pat. No. 8,604,440

SUMMARY

However, in the detector described in Patent Document 1, it is necessary to arrange many parts in a narrow internal space of the vacuum container, and manufacture is not easy.

An object of the present invention is to provide a thin high-energy ray detector that can be easily manufactured.

An embodiment of the present invention is a high-energy ray detector. The high-energy ray detector includes (1) a first electron multiplier including one or more micro-channel plates each configured to emit electrons by interaction with an incident high-energy ray, and multiply and output the electrons; (2) a second electron multiplier including one or more micro-channel plates each configured to emit electrons by interaction with an incident high-energy ray, and multiply and output the electrons; and (3) an electron collector configured to be transmissive for the high-energy ray, collect the electrons multiplied and output from each of the first electron multiplier and the second electron multiplier, and output an electric pulse signal, and the first electron multiplier, the electron collector, and the second electron multiplier are arranged in this order along a predetermined direction.

An embodiment of the present invention is a high-energy ray detector. The high-energy ray detector includes a plurality of detection units arranged along a predetermined direction, and each detection unit is constituted by an electron multiplier including one or more micro-channel plates each configured to emit electrons by interaction with an incident high-energy ray, and multiply and output the electrons, and an electron collector configured to be transmissive for the high-energy ray, collect the electrons multiplied and output from the electron multiplier, and output an electric pulse signal, being arranged along the predetermined direction.

In the above configuration, the high-energy ray to be detected by the high-energy ray detector is a γ-ray, an X-ray (in particular a hard X-ray), or a neutron ray.

An embodiment of the present invention is a tomographic image acquisition apparatus. The tomographic image acquisition apparatus is an apparatus configured to acquire a tomographic image of an object placed in a measurement space, and includes the high-energy ray detector of the above configuration as each of a plurality of detectors provided around the measurement space to detect the high-energy ray.

The high-energy ray detector according to the embodiments of the present invention is thin and can be easily manufactured.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DETAILED DESCRIPTION

Hereinafter, embodiments of a high-energy ray detector and a tomographic image acquisition apparatus will be described in detail with reference to the accompanying drawings. In the description of the drawings, the same elements will be denoted by the same reference signs, without redundant description. Further, the present invention is not limited to these examples.

Figure 1:
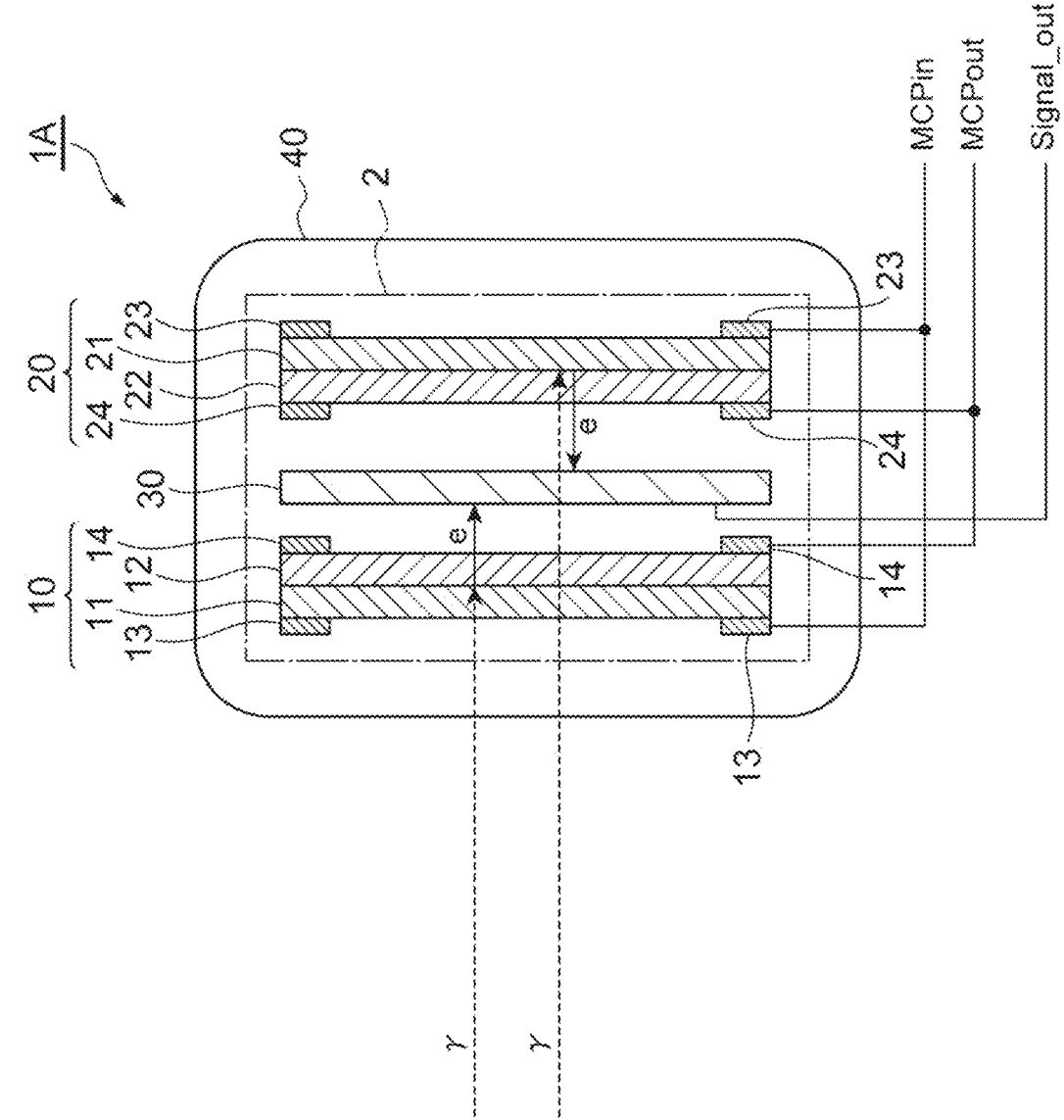
FIG. 1 is a view illustrating a configuration of a high-energy ray detector of a first embodiment.

FIG. 1 is a view illustrating a configuration of a high-energy ray detector 1A of a first embodiment. The high-energy ray detector 1A includes one detection unit 2 in a vacuum container 40. The detection unit 2 includes a first electron multiplier 10, a second electron multiplier 20, and an electron collector 30.

Each of the first electron multiplier 10 and the second electron multiplier 20 includes one or more micro-channel plates (MCPs) each configured to emit electrons by interaction with an incident high-energy ray (γ-ray, X-ray (in particular hard X-ray), or neutron ray), and multiply and output the electrons. Each of the first electron multiplier 10 and the second electron multiplier 20 preferably has a configuration in which the plurality of MCPs are stacked in order to obtain a sufficient electron multiplication factor. For example, in the case of a configuration in which two MCPs are stacked, it is possible to set the electron multiplication factor to about $10^6$.

In the present embodiment, the first electron multiplier 10 includes MCPs 11 and 12 as two stacked MCPs, and the second electron multiplier 20 includes MCPs 21 and 22 as two stacked MCPs. In the first electron multiplier 10 and the second electron multiplier 20, in one example, a thickness of one MCP is 0.2 mm, a thickness of the electron collector is 0.1 mm, and the MCP and the electron collector are arranged at an interval of 0.1 mm. In this case, a thickness of the detection unit including the first electron multiplier 10 and the second electron multiplier 20 is as thin as 1.1 mm.

In the case of detecting the γ-ray or X ray as the high-energy ray, a base material of each MCP is made of, for example, a glass material containing lead with high stopping power for the γ-rays or X rays. In the case of detecting the neutron ray as the high-energy ray, a base material of each MCP is made of, for example, a glass material containing a material (B, Li, Gd, or the like) which emits electrons by interaction with the neutrons.

The electron collector 30 is transmissive for the high-energy ray. The electron collector 30 collects the electrons multiplied and output from each of the first electron multiplier 10 and the second electron multiplier 20, and outputs an electric pulse signal. The electron collector 30 is an anode electrode. The electron collector 30 has, for example, a flat plate shape.

The first electron multiplier 10, the electron collector 30, and the second electron multiplier 20 are arranged in this order along a predetermined direction. That is, the electron collector 30 is provided between the first electron multiplier 10 and the second electron multiplier 20.

In the stacked body of the MCPs 11 and 12 of the first electron multiplier 10, an input-side electrode 13 is provided on a surface far from the electron collector 30, and an output-side electrode 14 is provided on a surface close to the electron collector 30. A potential of the output-side electrode 14 is set to be higher than a potential of the input-side electrode 13 and is set to be lower than a potential of the electron collector 30.

In the stacked body of the MCPs 21 and 22 of the second electron multiplier 20, an input-side electrode 23 is provided on a surface far from the electron collector 30, and an output-side electrode 24 is provided on a surface close to the electron collector 30. A potential of the output-side electrode 24 is set to be higher than a potential of the input-side electrode 23 and is set to be lower than the potential of the electron collector 30.

The set potential of the input-side electrode 13 and the set potential of the input-side electrode 23 may be the same with each other. The set potential of the output-side electrode 14 and the set potential of the output-side electrode 24 may be the same with each other. For example, the electron collector 30, which is the anode electrode, is set to a ground potential (0 V), a potential MCPin of the input-side electrode 13 and the input-side electrode 23 is set to −2.1 kV, and a potential MCPout of the output-side electrode 14 and the output-side electrode 24 is set to −0.1 kV.

A window portion of the vacuum container 40 which allows the high-energy ray to be incident into the inside thereof is transmissive for the high-energy ray. Assuming that the first electron multiplier 10 is arranged on the side close to the window portion, the high-energy ray incident to the inside of the vacuum container 40 from the window portion first reaches the first electron multiplier 10. At this time, when electrons are emitted from the MCPs 11 and 12 of the first electron multiplier 10 by the interaction with the high-energy ray, the electrons are multiplied by the MCPs 11 and 12, the multiplied electrons reach the electron collector 30 from the first electron multiplier 10, and the electron collector 30 outputs the electric pulse signal Signal_out.

When the high-energy ray incident to the inside of the vacuum container 40 does not interact in the MCPs 11 and 12 of the first electron multiplier 10, the high-energy ray passes through the first electron multiplier 10 and the electron collector 30 and reaches the second electron multiplier 20. At this time, when electrons are emitted from the MCPs 21 and 22 of the second electron multiplier 20 by the interaction with the high-energy ray, the electrons are multiplied by the MCPs 21 and 22, the multiplied electrons reach the electron collector 30 from the second electron multiplier 20, and the electron collector 30 outputs the electric pulse signal Signal_out.

In the above configuration, the efficiency of high-energy ray detection is approximately doubled by employing the configuration in which the second electron multiplier 20 is provided in addition to the first electron multiplier 10 and the electron collector 30. Even when electrons are emitted in the electron collector 30 due to the interaction of the high-energy ray, the electrons are not multiplied, and thus, the electron collector 30 does not output an electric pulse signal.

The high-energy ray detector 1A does not require a scintillator and a Cherenkov radiator, and further, does not require a photoelectric conversion unit. It is sufficient if the first electron multiplier 10, the second electron multiplier 20, and the electron collector 30 are arranged in the vacuum container 40, and further, the first electron multiplier 10 and the second electron multiplier 20 may have the same configuration with each other, and thus, the high-energy ray detector 1A can be easily manufactured.

The electron collector 30, which is the anode electrode, may be a flat plate made of a single conductive material (metal), but in this case, it is preferable that the thickness be small in order to have sufficient transmissivity for the high-energy ray. The electron collector 30 is preferably a metal foil (for example, a Ti foil, an Al foil, a Cu foil, or the like).

Figure 2:
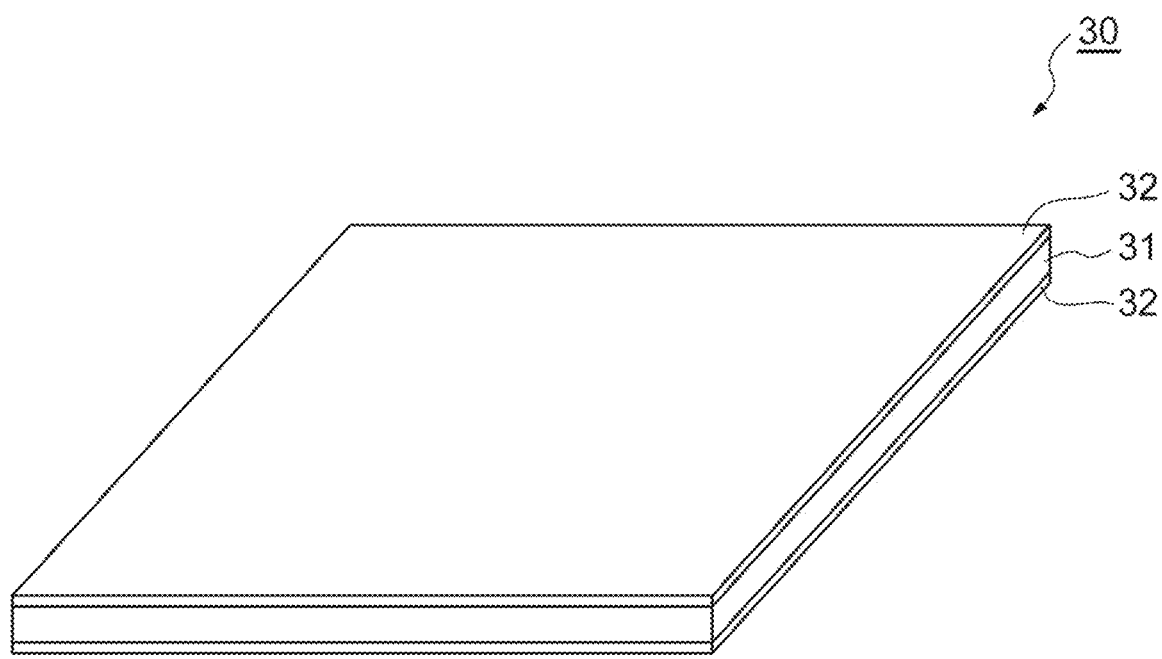
FIG. 2 is a view illustrating a configuration example of an electron collector.

As illustrated in FIG. 2, the electron collector 30 may include conductive portions 32 provided respectively on two principal surfaces of an insulating substrate 31. The insulating substrate 31 is preferably a resin substrate (for example, a polyimide substrate). The conductive portion 32 is preferably a metal film (for example, an Al film, a Cu film, or the like). In such a configuration, for example, a thickness of the polyimide substrate is 20 μm, and a thickness of the Cu film is 2 μm. With such a configuration, the electron collector 30 can have sufficient transmissivity for the high-energy ray.

Figure 3:
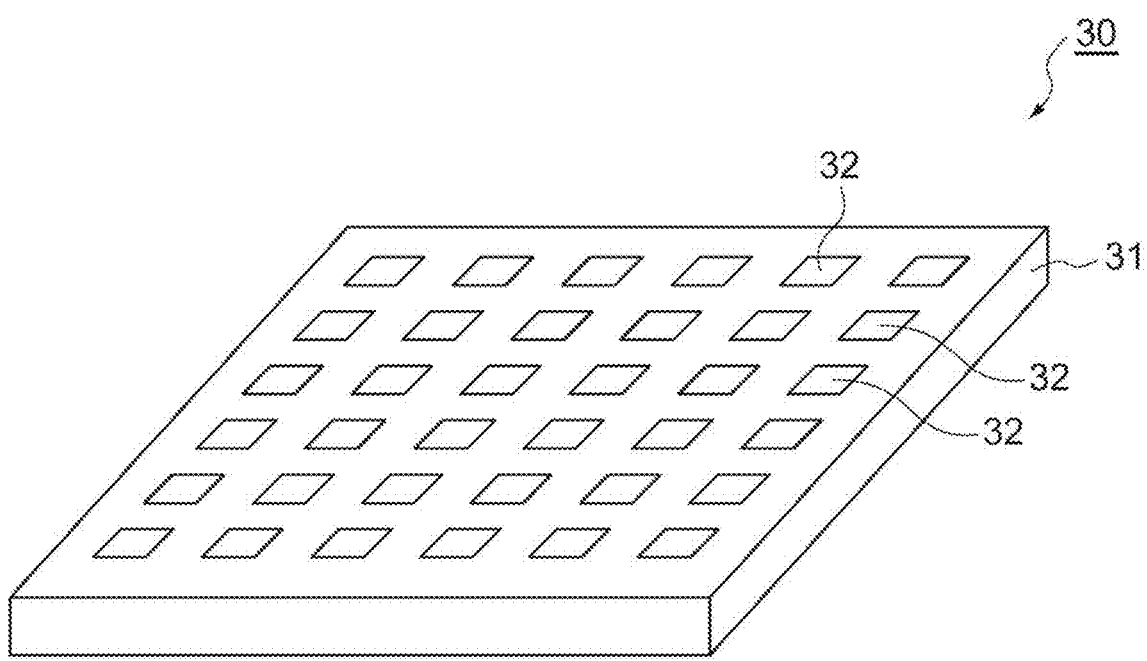
FIG. 3 is a view illustrating another configuration example of the electron collector.

As illustrated in FIG. 3, the electron collector 30 may have a plurality of conductive portions 32 arranged one-dimensionally or two-dimensionally on the principal surface of the insulating substrate 31. In FIG. 3, the 36 conductive portions 32 are arranged in six rows and six columns on the principal surface of the insulating substrate 31. Each of the plurality of conductive portions 32 collects electrons and outputs an electric pulse signal. A wiring for reading out the electric pulse signal to the outside from each of the plurality of conductive portions 32 may be formed on the principal surface of the insulating substrate 31, or may be embedded inside the insulating substrate 31.

Figure 4:
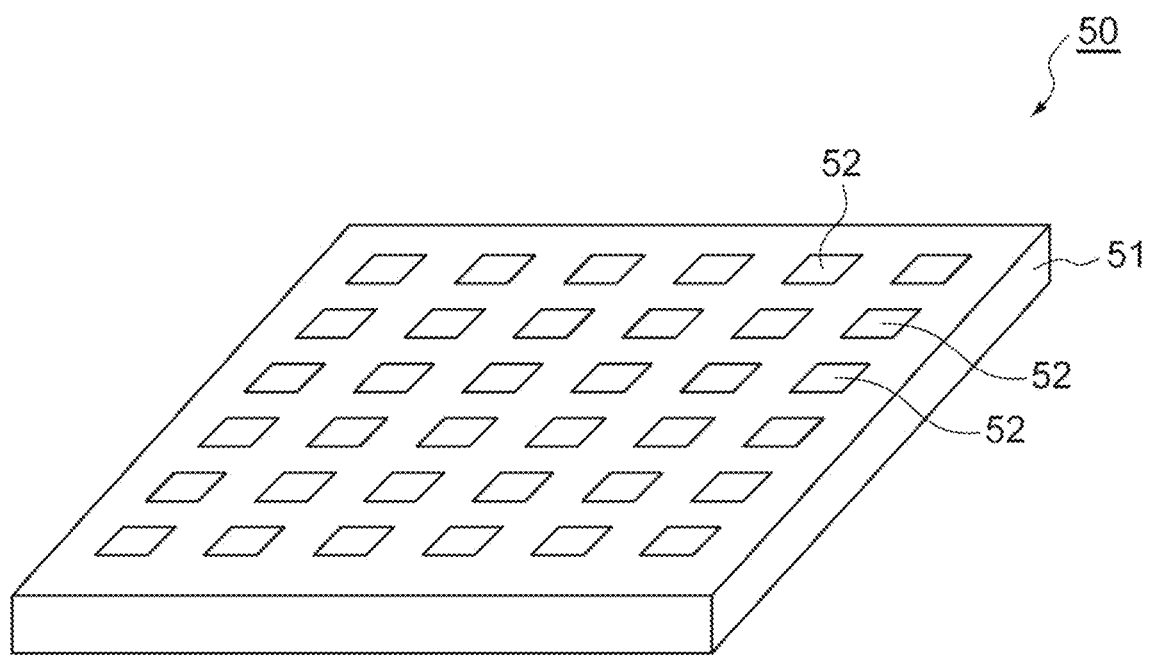
FIG. 4 is a view illustrating a configuration example of a signal readout element.
Figure 5:
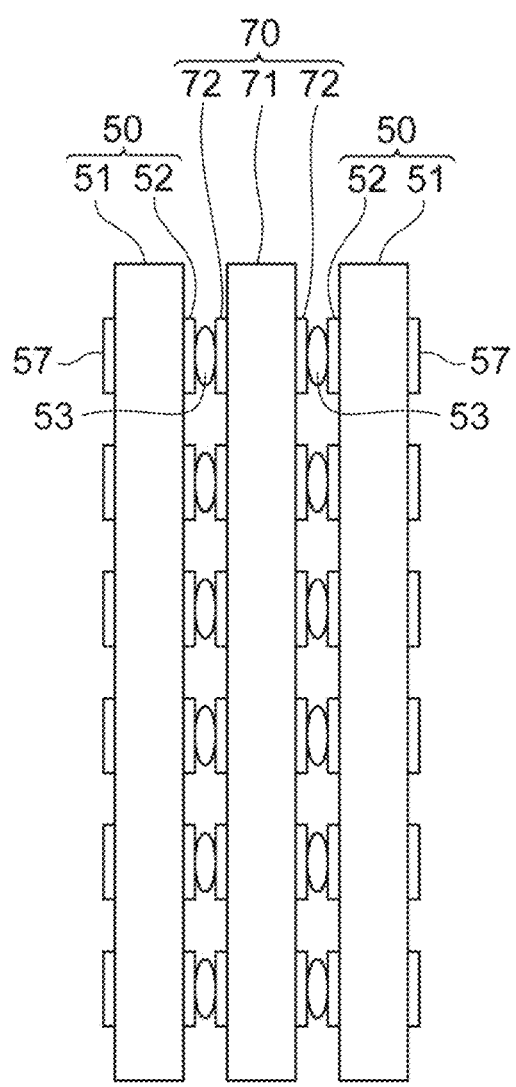
FIG. 5 is a view illustrating an electrical connection of the signal readout element of FIG. 4.

A signal readout element 50 illustrated in FIG. 4 and FIG. 5 may be used as an element to read out a plurality of electric pulse signals to the outside, instead of the electron collector 30 illustrated in FIG. 3. In the signal readout element 50, a plurality of conductive portions 57 receiving electrons from the MCP are arranged one-dimensionally or two-dimensionally on one principal surface of a semiconductor substrate 51, and further, a plurality of conductive portions 52 are arranged on the other principal surface. In order to supply power to the two signal readout elements 50 and read out signals from the two signal readout elements 50, for example, a power supply element 70 may be arranged between the two signal readout elements 50. In this case, conductive portions 72 on a substrate 71 of the power supply element 70 and the conductive portions 52 of the signal readout element 50 are electrically connected by, for example, bumps 53 as illustrated in FIG. 5.

Figure 6:
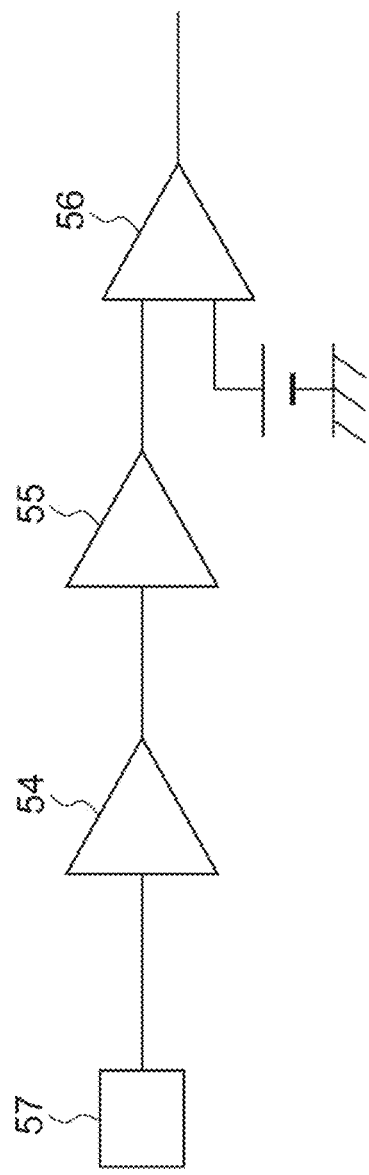
FIG. 6 is a diagram illustrating an example of a circuit configuration of a readout circuit in the signal readout element.

A readout circuit and a wiring for reading out the electric pulse signals from the respective conductive portions 57 to the outside through the power supply element 70 are formed on the semiconductor substrate 51 of the signal readout element 50. The readout circuit includes a charge amplifier 54, a shaping amplifier 55, and a lower level discriminator 56 as illustrated in FIG. 6.

The charge amplifier 54 converts a charge signal input from the MCP through the conductive portion 57 into a current signal. The shaping amplifier 55 receives the current signal output from the charge amplifier 54, shapes a waveform of the current signal, amplifies the signal, and outputs the amplified signal as a voltage signal. The lower level discriminator (LLD) 56 receives the voltage signal output from the shaping amplifier 55, and outputs a digital pulse having a predetermined pulse height when a value of the voltage signal exceeds a predetermined threshold. An output signal of the LLD 56 is sent to a logic circuit to store an output timing. The signal output from the logic circuit is sent to an external circuit through the power supply element 70, and the signal is processed in the external circuit.

In addition, a plurality of the signal readout elements 50 may be provided for the single power supply element 70.

The electron collector in FIG. 3 to FIG. 5 has the plurality of conductive portions 32 or the plurality of conductive portions 57, that is, the plurality of anode electrodes. Such an electron collector can have a spatial resolution according to an arrangement pitch of the plurality of conductive portions. The MCP multiplies electrons in a channel having a diameter of 10 μm, for example, and thus, has a high spatial resolution. Therefore, for example, when the arrangement pitch of the conductive portions 32 in the electron collector 30 is 100 μm, it is possible to obtain a signal with a spatial resolution of 100 μm. In addition, a spatial resolution is limited to about 2 mm in a high-energy ray detector using a scintillator or a Cherenkov radiator since a size of the scintillator or Cherenkov radiator and spread of light from the scintillator or Cherenkov radiator to a photodetector determine the spatial resolution.

Figure 7:
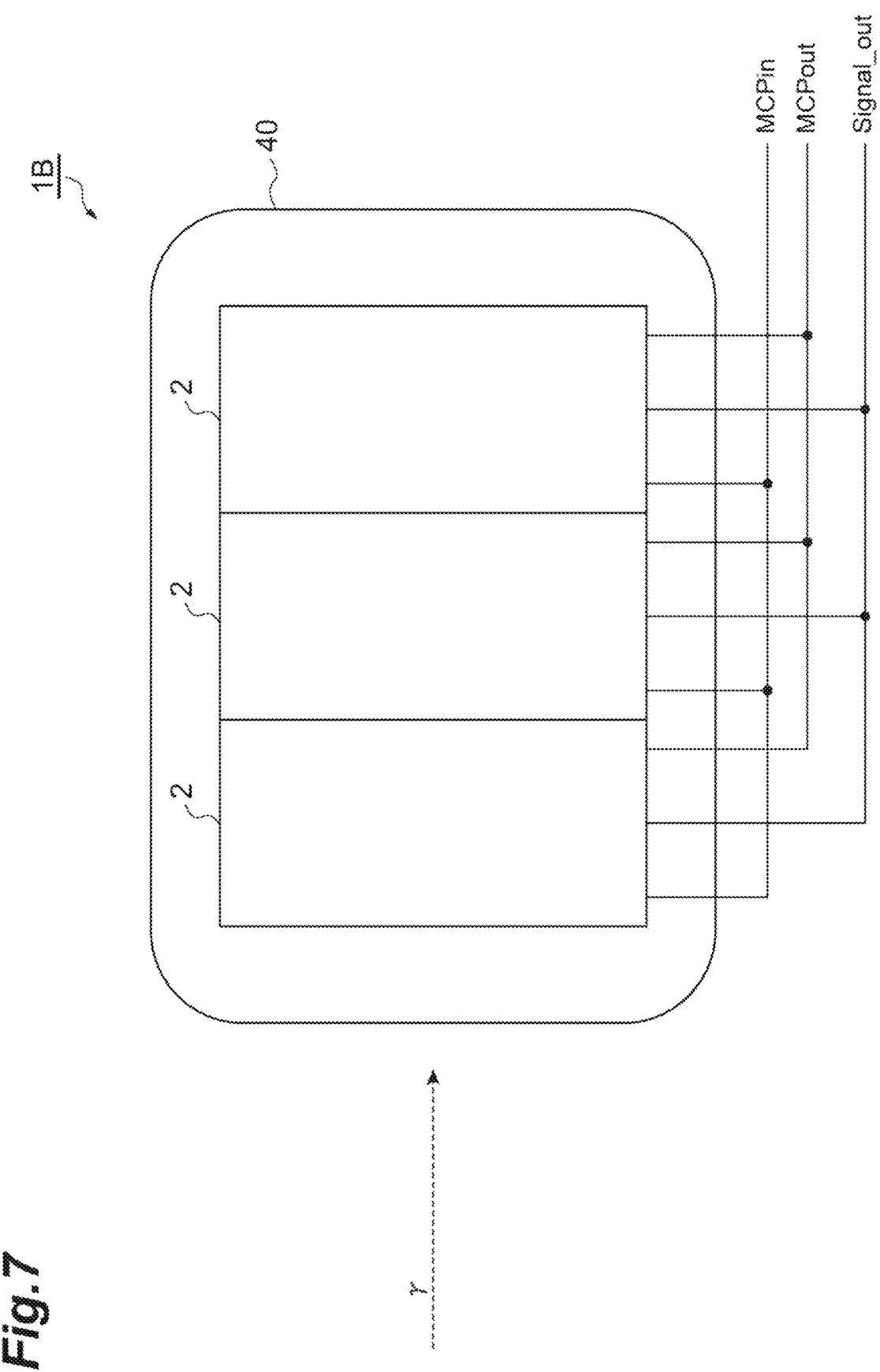
FIG. 7 is a view illustrating a configuration of a high-energy ray detector of a second embodiment.

FIG. 7 is a view illustrating a configuration of a high-energy ray detector 1B of a second embodiment. The high-energy ray detector 1B includes a plurality of (three in the drawing) detection units 2 in the vacuum container 40. In each of the detection units 2, a first electron multiplier 10, an electron collector 30, and a second electron multiplier 20 are stacked and arranged in this order along a predetermined direction similarly to the case of the first embodiment. Further, the plurality of detection units 2 are stacked and arranged along the predetermined direction. A potential MCPin for input-side electrodes 13 and 23 and a potential MCPout for output-side electrodes 14 and 24 are applied to each of the detection units 2 (see FIG. 1). Electric pulse signals Signal_out are output from the electron collectors 30 of the plurality of detection units 2 to a common signal line.

Since the high-energy ray detector 1B has such a stacked structure, there is a case where a high-energy ray can be detected by the second detection unit 2 of the next stage even when the first detection unit 2 arranged at the position closest to the window portion has failed to detect the high-energy ray. Further, there is a case where a high-energy ray can be detected by the third detection unit 2 at the final stage even when the first and second detection units 2 have failed to detect the high-energy ray. Therefore, the efficiency of high-energy ray detection can be enhanced according to such a configuration.

Figure 8:
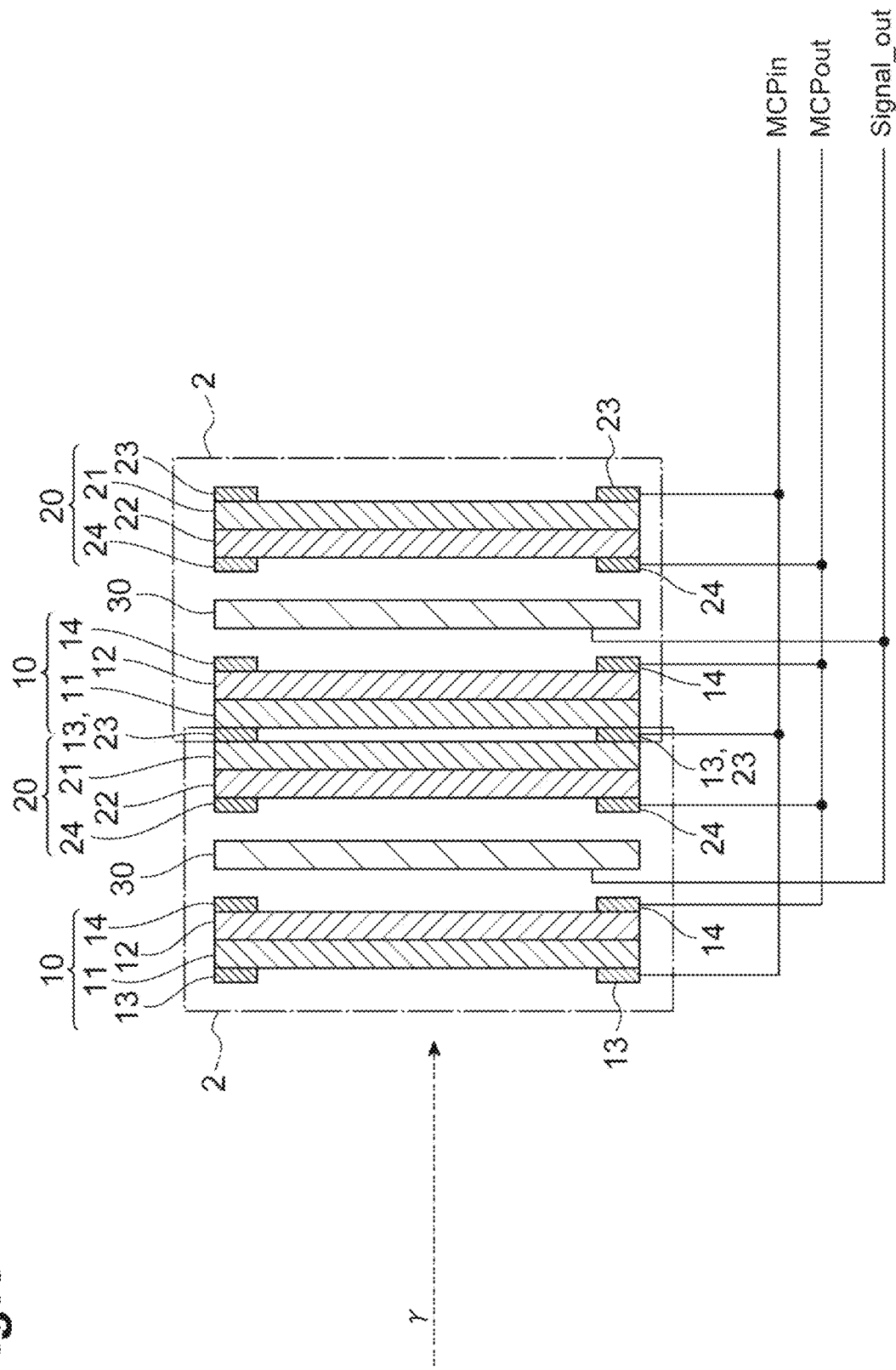
FIG. 8 is a view illustrating a configuration example of two adjacent detection units among a plurality of detection units of the high-energy ray detector.
Figure 9:
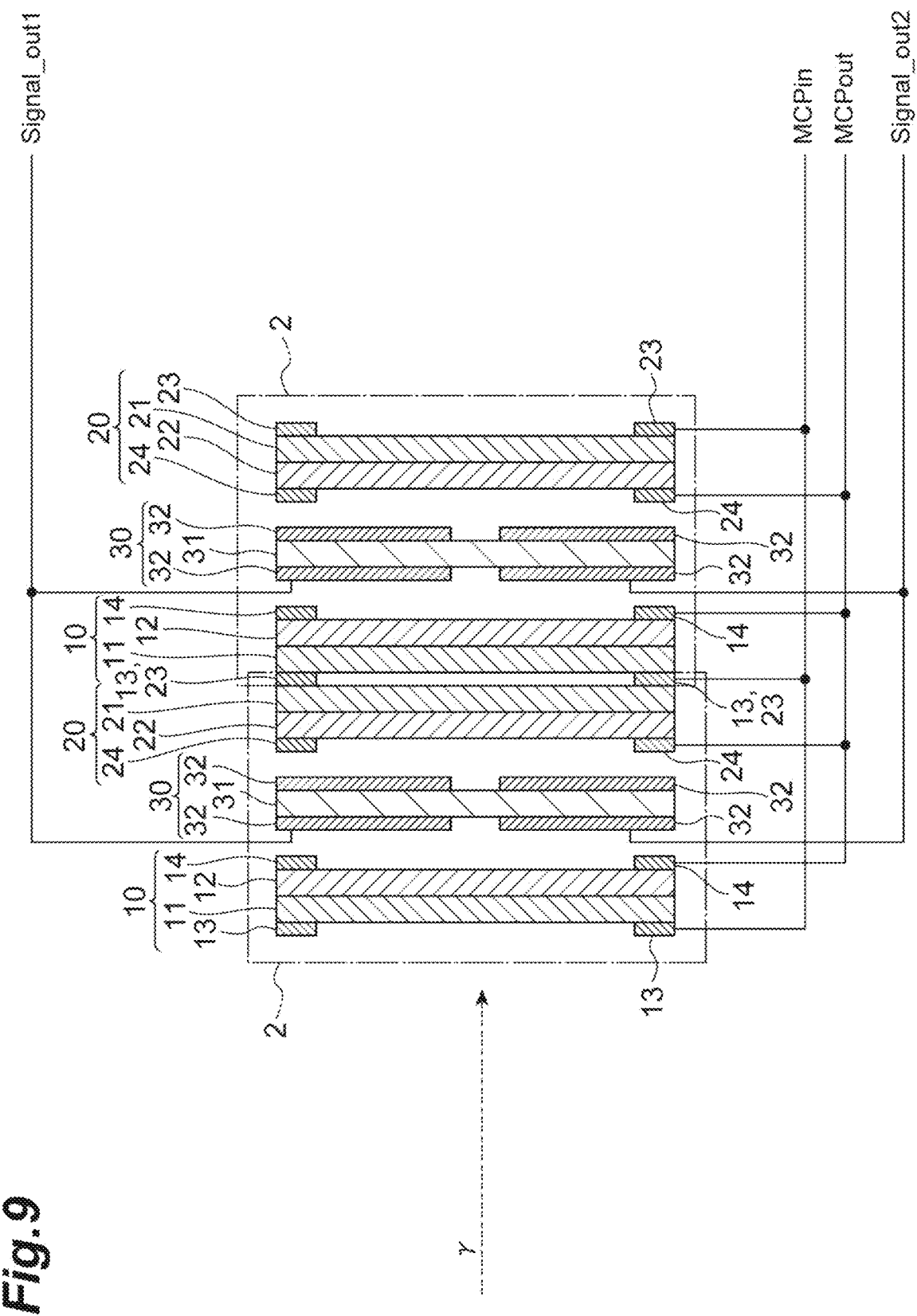
FIG. 9 is a view illustrating another configuration example of two adjacent detection units among the plurality of detection units of the high-energy ray detector.

FIG. 8 and FIG. 9 are views illustrating configuration examples of two adjacent detection units 2 among the plurality of detection units 2 of the high-energy ray detector 1B. FIG. 8 illustrates the case where the electron collector 30 in each of the detection units 2 is one anode electrode. FIG. 9 illustrates the case where the electron collector 30 in each of the detection units 2 is configured to include a plurality of conductive portions 32 on the insulating substrate 31. The input-side electrode 23 of the second electron multiplier 20 of the detection unit 2 of the previous stage and the input-side electrode 13 of the first electron multiplier 10 of the detection unit 2 of the subsequent stage can be set to the same potential, and thus, discharge does not occur even when both the electrodes are arranged close to each other. Further, the input-side electrode 23 of the second electron multiplier 20 of the detection unit 2 of the previous stage and the input-side electrode 13 of the first electron multiplier 10 of the detection unit 2 of the subsequent stage can be also configured as a common electrode. Therefore, not only a thickness of the high-energy ray detector 1B can be reduced but also a wiring can be easily configured.

In addition, in the configuration of the high-energy ray detector 1B illustrated in FIG. 7 to FIG. 9, the electric pulse signals Signal_out are output from the electron collectors 30 of the plurality of detection units 2 to the common signal line. On the other hand, the electric pulse signal Signal_out may be output independently from the electron collector 30 of each of the detection units 2. In this manner, it is possible to know which detection unit 2 among the plurality of detection units 2 has detected the high-energy ray. That is, it becomes possible to measure a detection position in a flight direction of the high-energy ray (measure a depth of interaction (DOI)). Therefore, when the high-energy ray detector 1B is used in a TOF-PET apparatus, an annihilation position on a coincidence line can be obtained more accurately.

Figure 10:
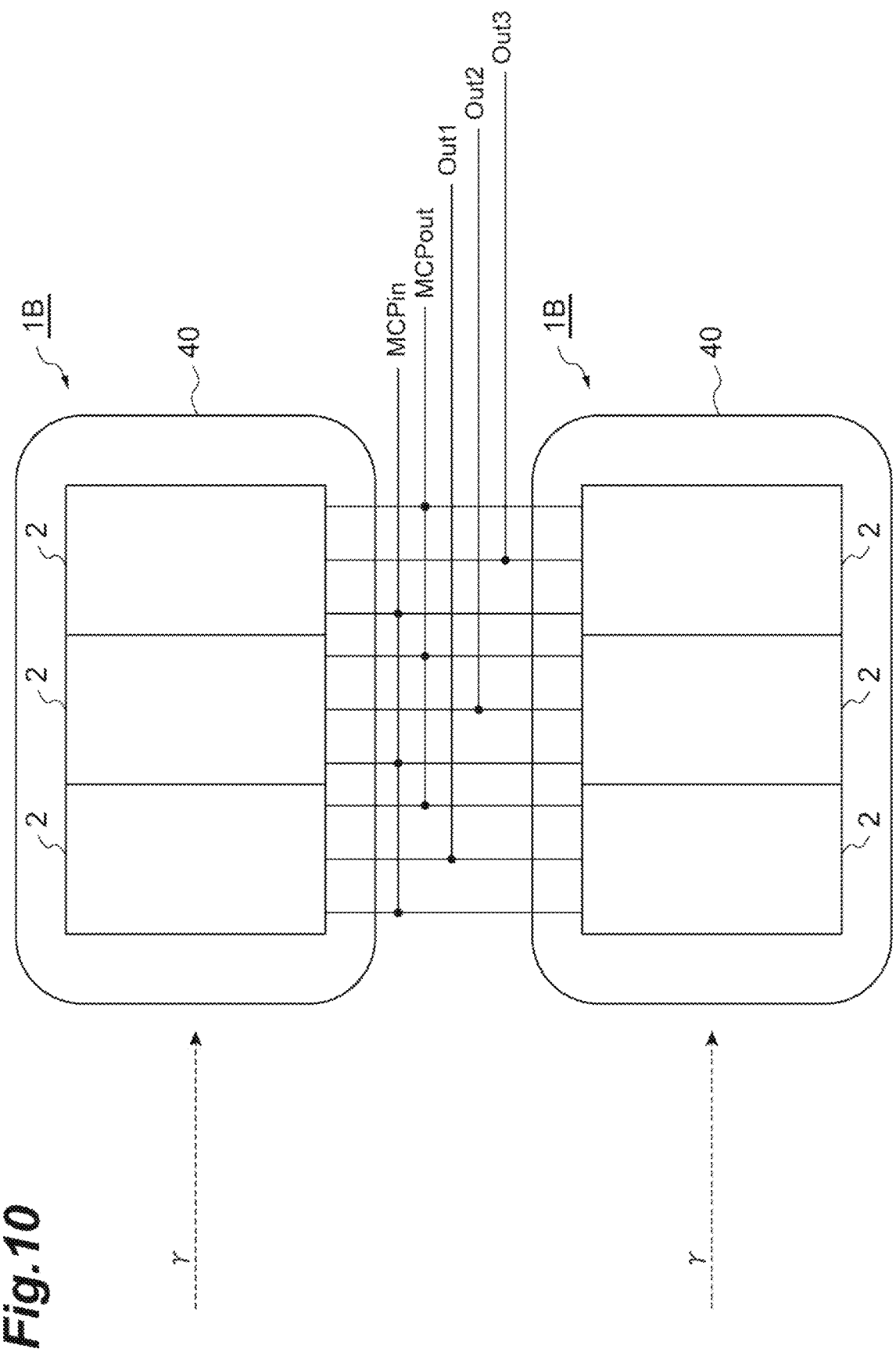
FIG. 10 is a view illustrating a configuration in which a plurality of high-energy ray detectors are arranged in parallel.

FIG. 10 is a view illustrating a configuration in which a plurality of high-energy ray detectors 1B are arranged in parallel. In the configuration illustrated in the drawing, the plurality of (two in the drawing) high-energy ray detectors 1B illustrated in FIG. 7 are arranged in parallel, and an electric pulse signal Out1 is output to a common signal line from the electron collector 30 of the first detection unit 2 of each of the high-energy ray detectors 1B, an electric pulse signal Out2 is output to a common signal line from the electron collector 30 of the second detection unit 2 of each of the high-energy ray detectors 1B, and an electric pulse signal Out3 is output to a common signal line from the electron collector 30 of the third detection unit 2 of each of the high-energy ray detectors 1B. In such a configuration, not only DOI measurement is possible, but also a detectable range of a high-energy ray is expanded.

Figure 11:
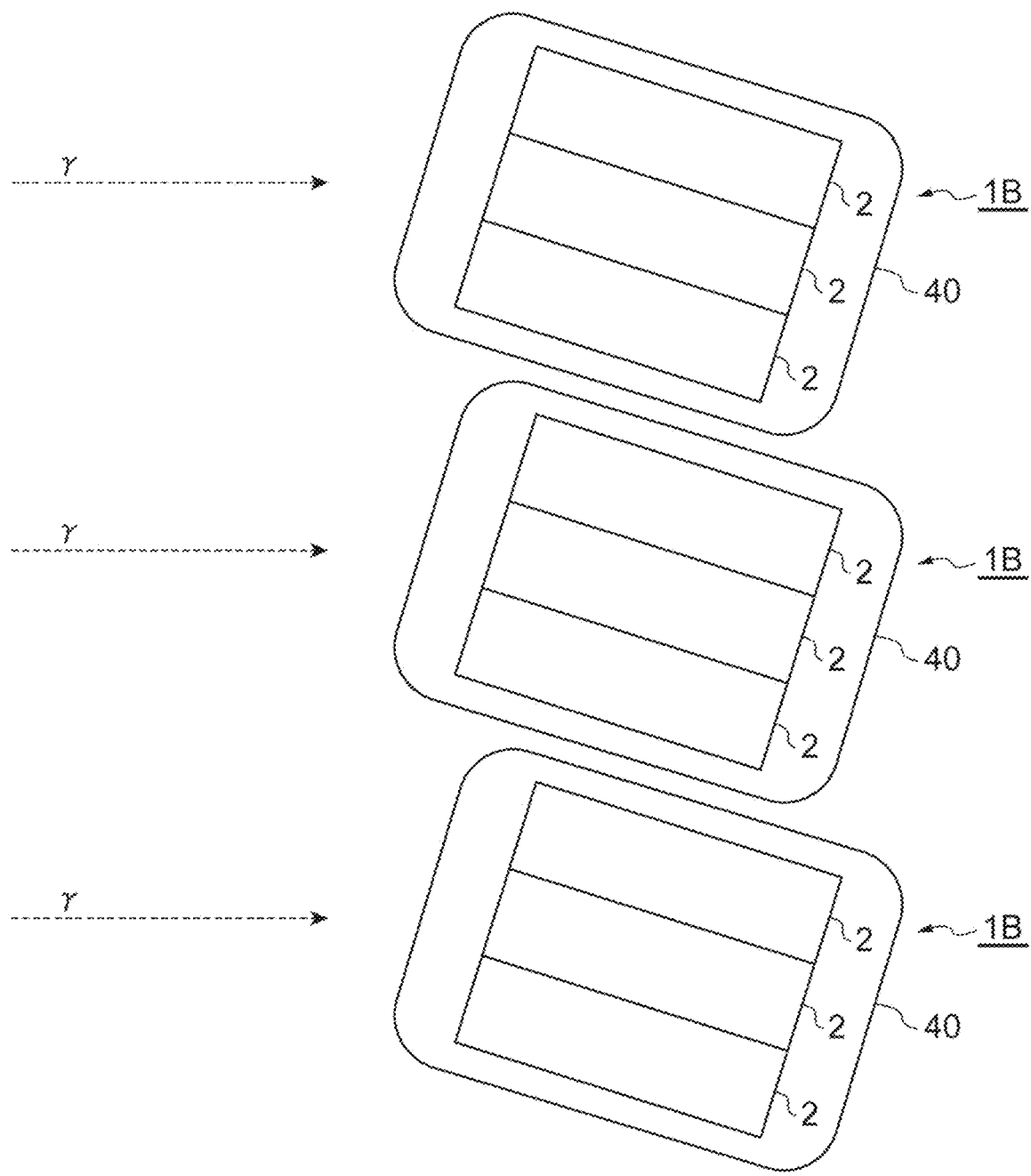
FIG. 11 is a view illustrating another configuration in which the plurality of high-energy ray detectors are arranged in parallel.

FIG. 11 is a view illustrating another configuration in which the plurality of high-energy ray detectors 1B are arranged in parallel. Although each of the high-energy ray detectors 1B is arranged such that the high-energy ray is incident to the MCP from a vertical direction in the configuration illustrated in FIG. 10, each of the high-energy ray detectors 1B is arranged such that the high-energy ray is incident to the MCP from an oblique direction in the configuration illustrated in FIG. 11. That is, a direction of stacking of the plurality of detection units 2 in each of the high-energy ray detectors 1B is different from the incident direction of the high-energy ray. With such a configuration, it is possible to reduce an insensitive region.

Figure 12:
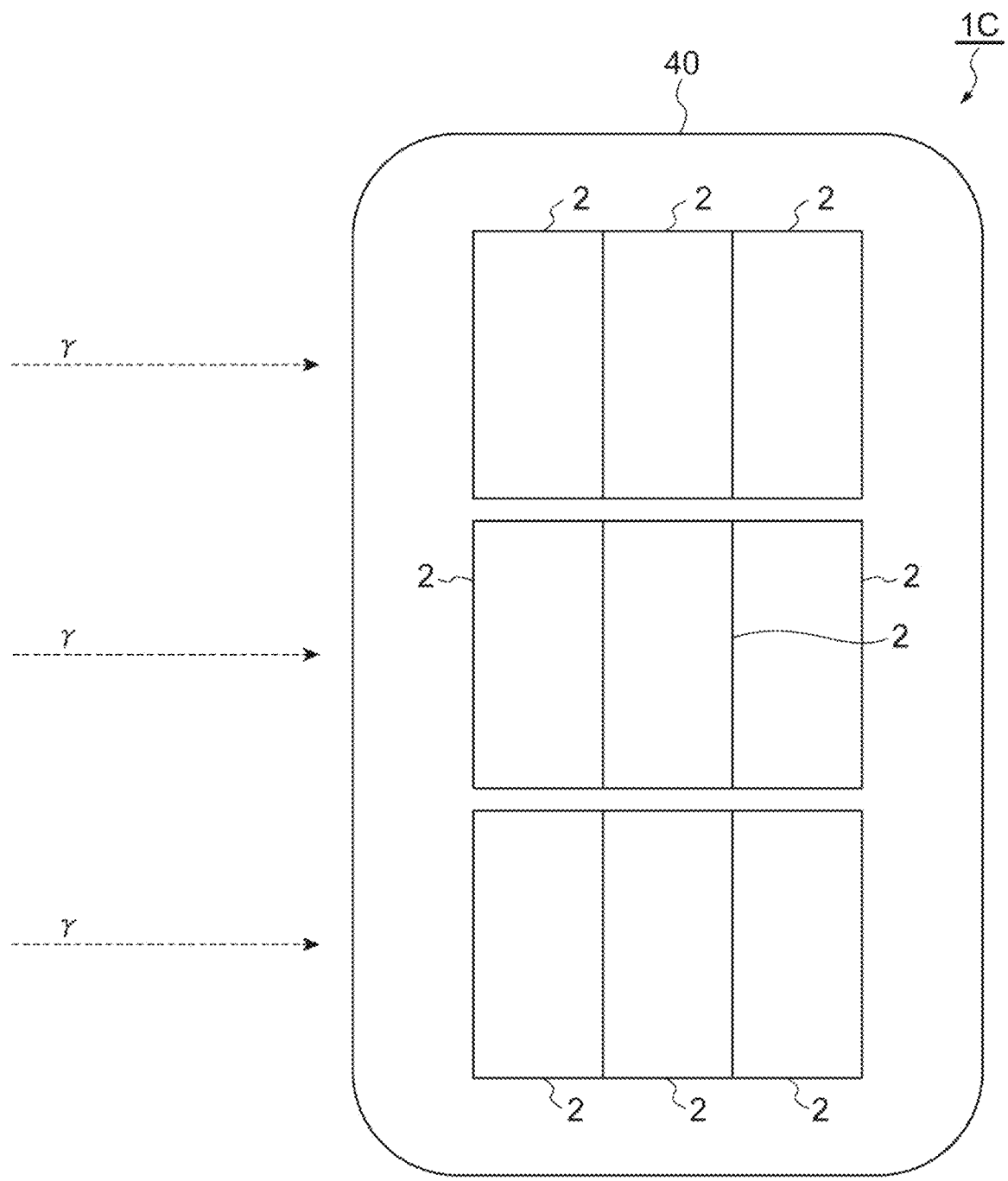
FIG. 12 is a view illustrating a configuration of a high-energy ray detector of a third embodiment.

FIG. 12 is a view illustrating a configuration of a high-energy ray detector 1C of a third embodiment. The high-energy ray detector 1C includes a plurality of (nine in the drawing) detection units 2 in the vacuum container 40. Although the high-energy ray detector 1B illustrated in FIG. 7 has the configuration in which the plurality of detection units 2 are stacked, the high-energy ray detector 1C illustrated in FIG. 12 has a configuration in which the configurations in which the plurality of detection units 2 are stacked are further arranged in parallel. In the high-energy ray detector 1C, not only DOI measurement is possible, but also a detectable range of a high-energy ray is expanded.

Further, when compared with the configuration illustrated in FIG. 10, the high-energy ray detector 1C illustrated in FIG. 12 is similar in terms that the configurations in which the plurality of detection units 2 are stacked are further arranged in parallel, but is different in terms of having the parallel arrangement in addition to the stacked arrangement in the single vacuum container 40. Therefore, an interval in the parallel arrangement can be narrowed in the high-energy ray detector 1C, and thus, it is possible to reduce an insensitive region as compared with the configuration illustrated in FIG. 10.

Figure 13:
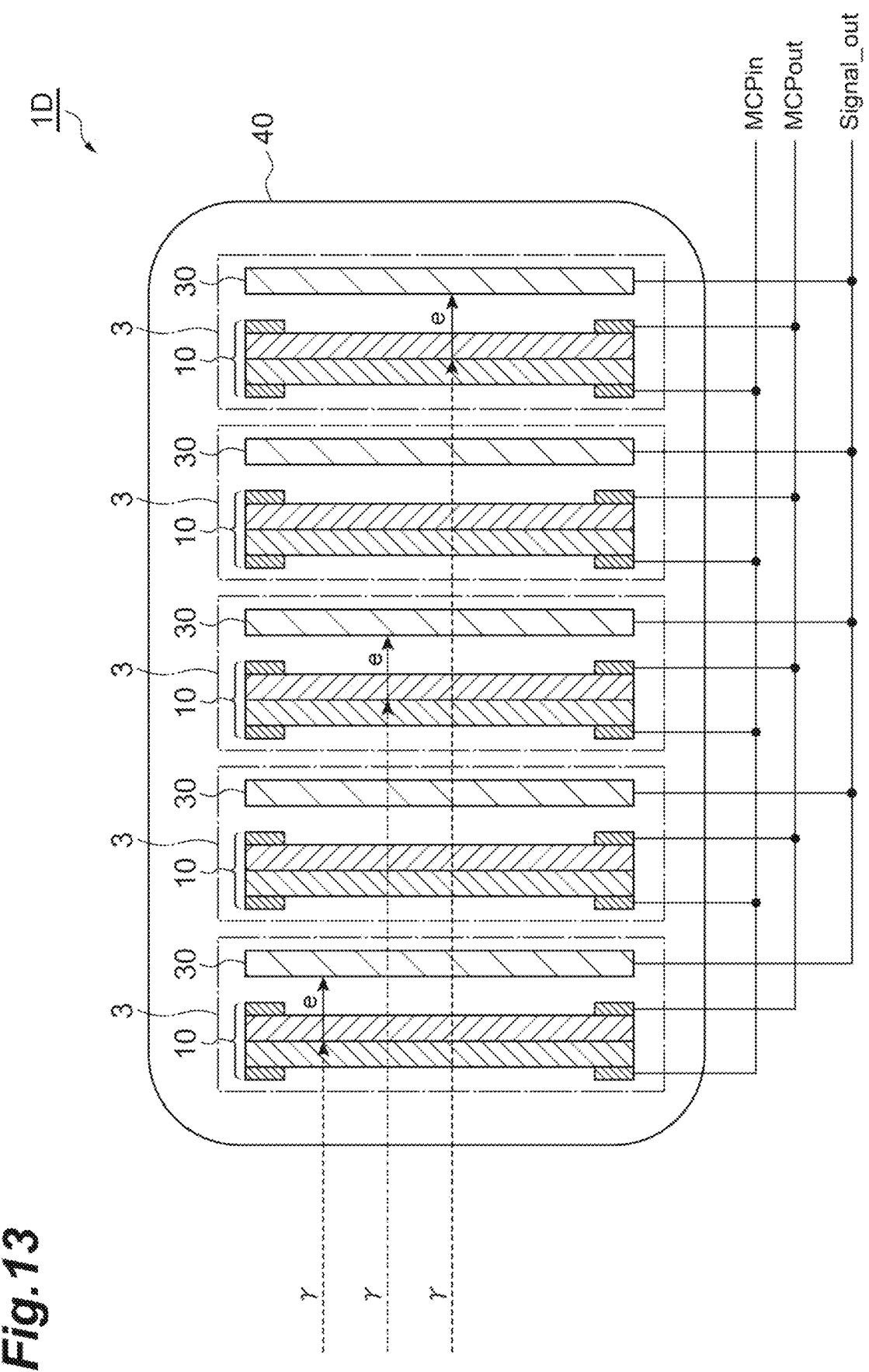
FIG. 13 is a view illustrating a configuration of a high-energy ray detector of a fourth embodiment.

FIG. 13 is a view illustrating a configuration of a high-energy ray detector 1D of a fourth embodiment. The high-energy ray detector 1D includes a plurality of (five in the drawing) detection units 3 stacked and arranged in the vacuum container 40 along a predetermined direction. Each of the detection units 3 includes an electron multiplier 10 and an electron collector 30. The electron multiplier 10 of each of the detection units 3 has the same configuration as the first electron multiplier 10 of the detection unit 2 described above. The electron collector 30 of each of the detection units 3 has the same configuration as the electron collector 30 of the detection unit 2 described above. Although the detection unit 2 described above includes the second electron multiplier 20 in addition to the first electron multiplier 10 and the electron collector 30, the detection unit 3 according to the fourth embodiment includes the electron multiplier 10 and the electron collector 30, and does not include a part corresponding to the second electron multiplier 20.

Since the high-energy ray detector 1D has such a stacked structure, there is a case where a high-energy ray can be detected by the second detection unit 3 of the next stage even when the first detection unit 3 arranged at the position closest to the window portion has failed to detect the high-energy ray. Further, there is a case where a high-energy ray can be detected by the third detection unit 3 even when the first and second detection units 3 have failed to detect the high-energy ray. Similarly, there is a case where a high-energy ray can be detected by the (n+1)-th detection unit 3 even when the first to n-th detection units 3 have failed to detect the high-energy ray. Therefore, the efficiency of high-energy ray detection can be enhanced according to such a configuration.

In addition, the high-energy ray detector 1D including the detection unit 3 of the fourth embodiment illustrated in FIG. 13 may have the same configuration as that of the specific example or modified examples described above with reference to FIG. 2 to FIG. 12.

The high-energy ray detector according to the present embodiment can be provided around a measurement space and used as a detector for detecting a high-energy ray, in a tomographic image acquisition apparatus configured to acquire a tomographic image of an object placed in the measurement space. Here, examples of the tomographic image acquisition apparatus include a PET apparatus, an X-ray CT apparatus, and a PET/CT apparatus. Further, examples of the PET apparatus also include a TOF-PET apparatus as well as a normal PET apparatus.

In the PET apparatus, the high-energy ray detector of the present embodiment detects a γ-ray generated with electron-positron annihilation in the object into which an RI source is introduced. In the X-ray CT apparatus, the high-energy ray detector of the present embodiment detects an X-ray output from an X-ray source and transmitted through the object. In the PET/CT apparatus, the high-energy ray detector of the present embodiment detects an X-ray output from an X-ray source and transmitted through the object, and detects a γ-ray generated with electron-positron annihilation in the object into which an RI source is introduced.

Figure 14:
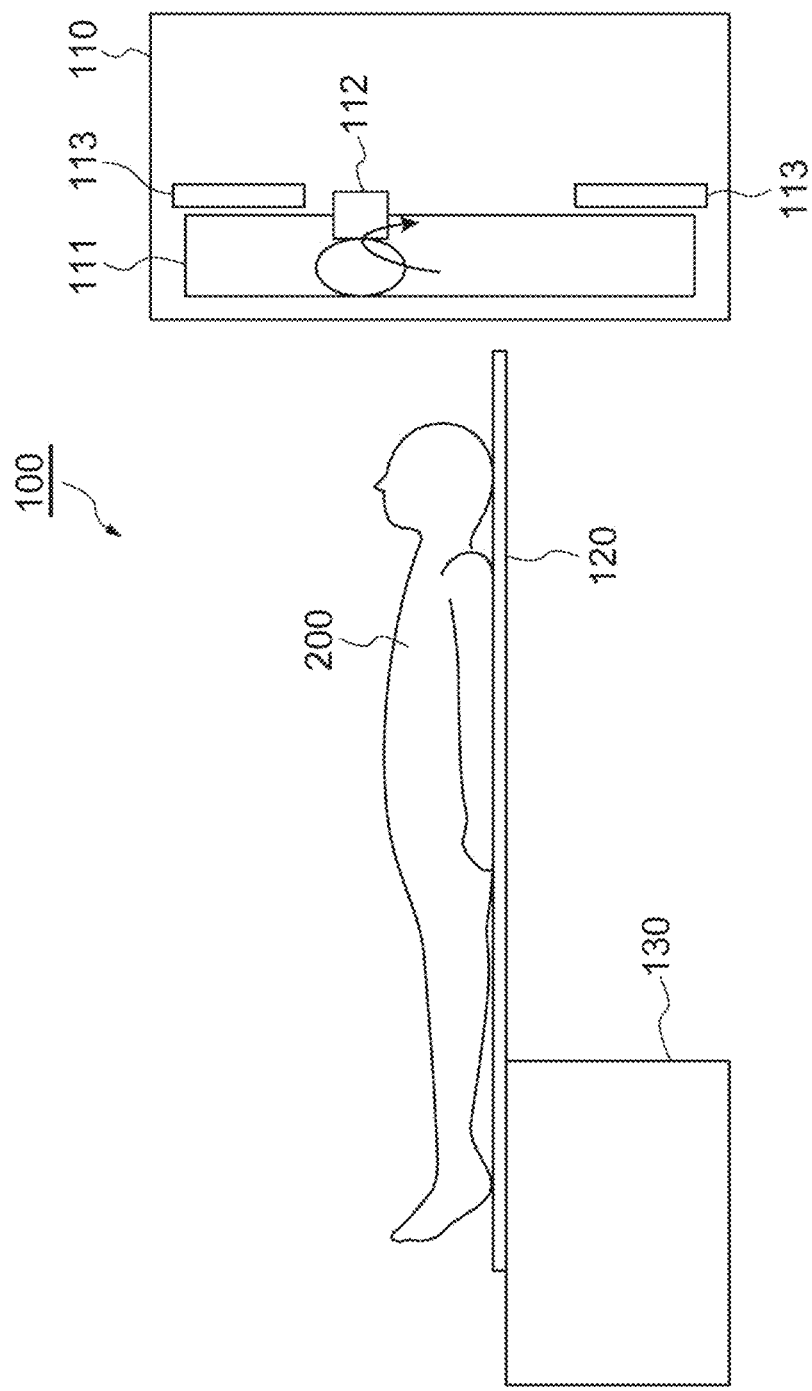
FIG. 14 is a view illustrating a configuration of a PET/CT apparatus.
Figure 15:
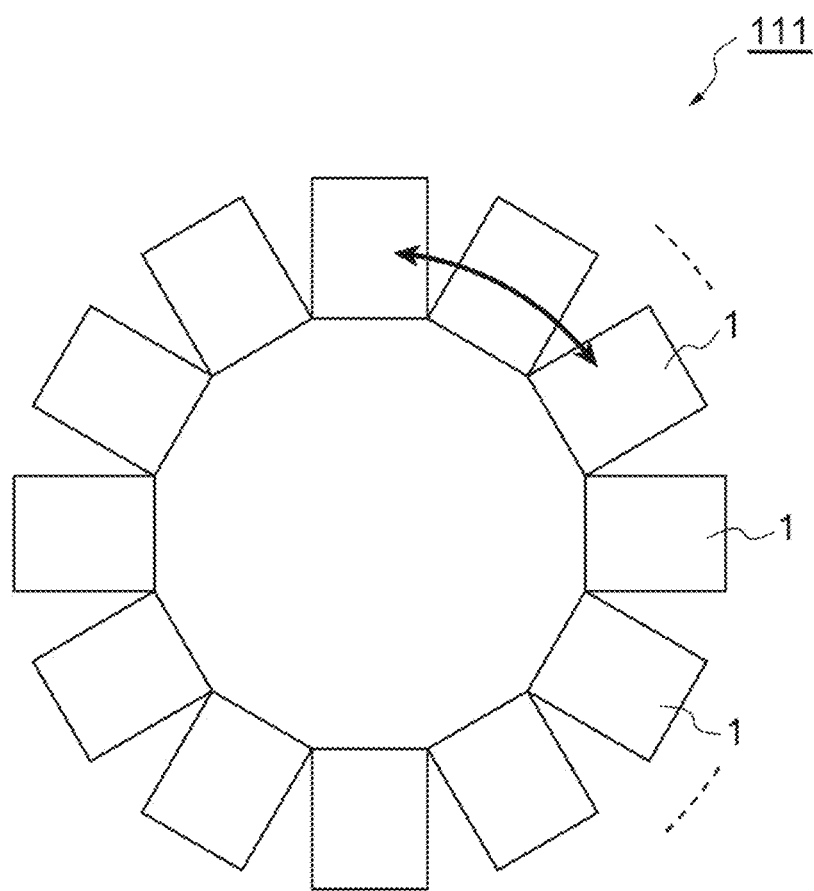
FIG. 15 is a view illustrating an arrangement of the high-energy ray detectors in a detector ring as viewed in an axial direction of the PET/CT apparatus.

FIG. 14 and FIG. 15 are views illustrating a configuration of a PET/CT apparatus 100. The PET/CT apparatus 100 includes a gantry 110, a table 120 and a drive unit 130. The gantry 110 includes a detector ring 111, an X-ray source 112, and an end shield 113.

FIG. 15 is a view illustrating an arrangement of the high-energy ray detectors 1 in the detector ring 111 as viewed in an axial direction of the PET/CT apparatus 100. The detector ring 111 includes the multiple high-energy ray detectors 1 which detect an X-ray or a γ-ray which is a high-energy ray arriving from a measurement space. The plurality of high-energy ray detectors 1 correspond to those of the above embodiments, and are arranged to surround the measurement space. The detector ring 111 preferably rotates about an axis to eliminate a dead space between the adjacent high-energy ray detectors 1 to improve sampling. It is sufficient to set an angle of the rotation to correspond to at least one high-energy ray detector including the dead space.

The X-ray source 112 may rotate inside the detector ring 111 or may rotate outside the detector ring 111. When the X-ray source 112 rotates inside the detector ring 111, the X-ray source 112 is retracted outside the detector ring 111 to a lateral side of the end shield 113 in a period during which X-ray CT scan is not performed. It is possible to acquire position information of the X-ray source 112, and thus, it is possible to perform measurement by simultaneously rotating the two or more X-ray sources 112. For example, when X-ray sources with different tube voltages are used, the X-ray measurement with a plurality of energy regions is possible, and thus, material distribution inside a body can be measured more accurately.

An object 200 into which a PET drug (RI source) and a CT contrast agent have been administered is placed on the table 120. The table 120 is driven by the drive unit 130 and is movable in a vertical direction and in an axial direction. The object 200 placed on the table 120 is transported to the measurement space inside the detector ring 111 to be subjected to X-ray CT scan and PET scan.

Figure 16:
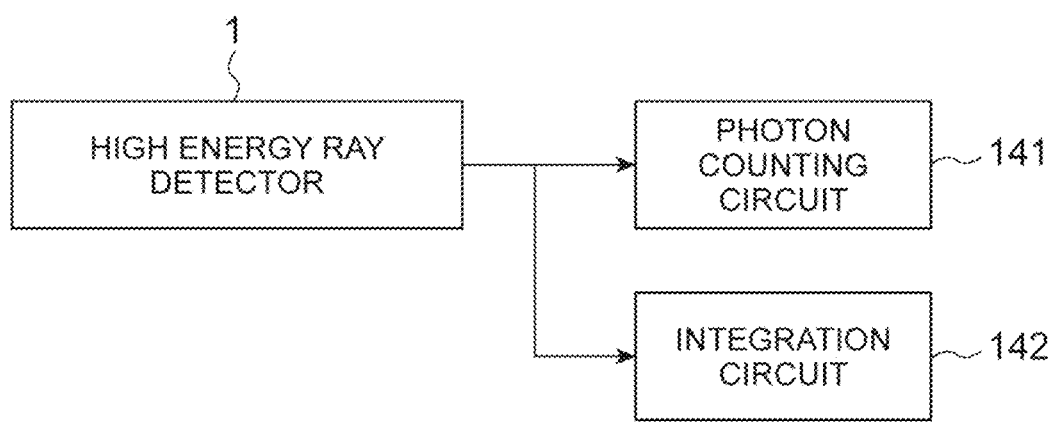
FIG. 16 is a diagram for describing processing of an electric pulse signal output from the high-energy ray detector in the detector ring of the PET/CT apparatus.

FIG. 16 is a diagram for describing processing of an electric pulse signal output from the high-energy ray detector 1 in the detector ring 111 of the PET/CT apparatus 100. In this configuration example, a photon counting circuit 141 or an integration circuit 142 is selectively used as a circuit for processing the electric pulse signal output from the high-energy ray detector 1. The photon counting circuit 141 is configured to be capable of distinguishing and counting individual photon detection events (photon counting). Further, the integration circuit 142 is configured to be capable of summing signal values over a certain period of time without distinguishing between individual photon detection events. The photon counting circuit 141 and the integration circuit 142 can be used selectively depending on the magnitude of the electric pulse signal output from the high-energy ray detector 1.

For example, during the PET scan in which the high-energy ray detector 1 detects a γ-ray, photon counting can be performed by processing the electric pulse signal output from the high-energy ray detector 1 using the photon counting circuit 141. During a period of the X-ray CT scan in which the high-energy ray detector 1 detects an X-ray, it can be used as photon counting CT when the processing is performed by the photon counting circuit 141, and it can be used as normal CT when the processing is performed by the integration circuit 142.

Figure 17:
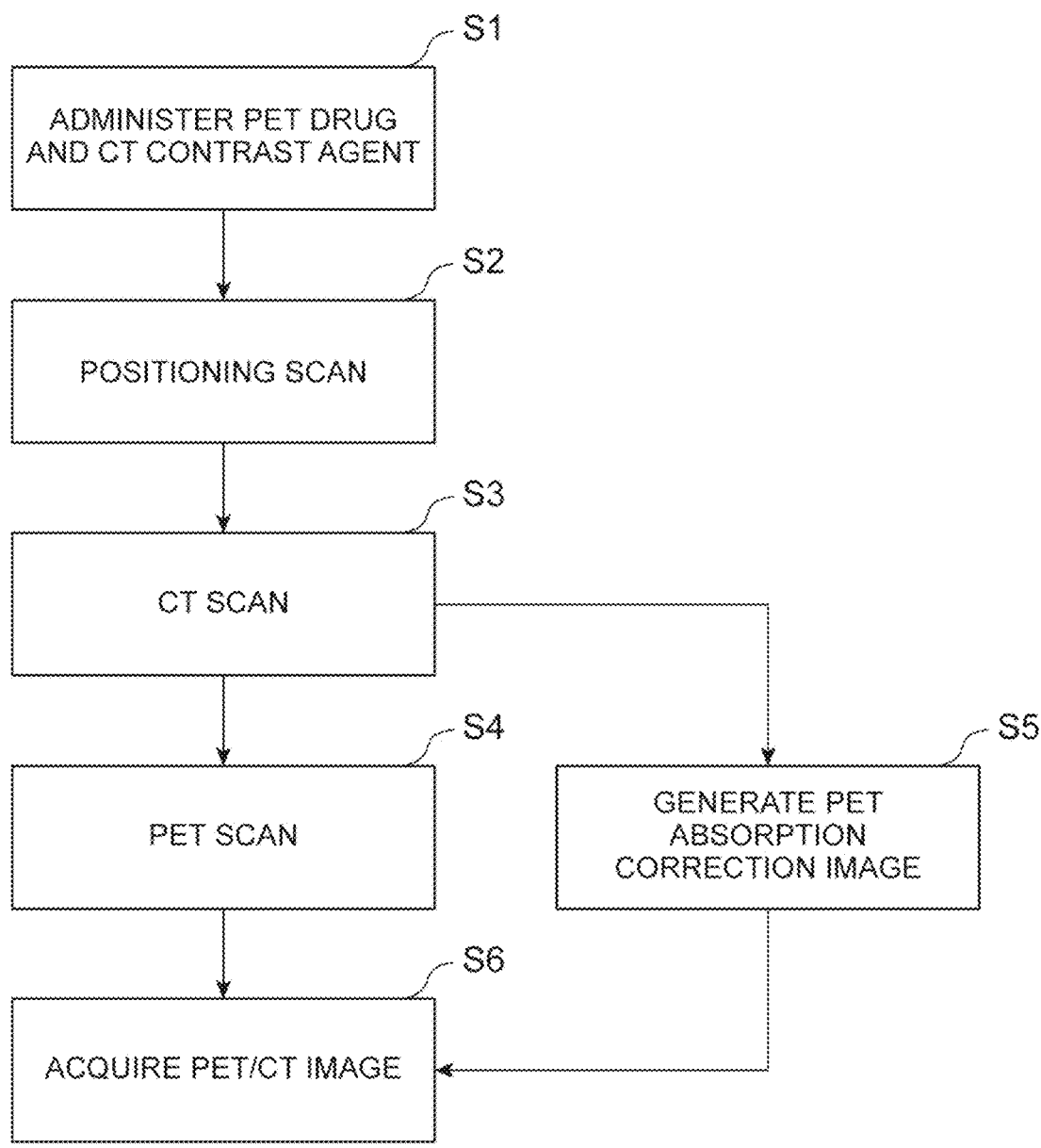
FIG. 17 is a flowchart illustrating an operation example of the PET/CT apparatus.

FIG. 17 is a flowchart illustrating an operation example of the PET/CT apparatus 100. In this operation example, the PET drug (RI source) and the CT contrast agent are administered to the object (Step S1), and the object is placed on the table 120 and transported to the measurement space. X-ray CT scan for positioning is performed on the object placed in the measurement space (Step S2). Subsequently, the object is subjected to X-ray CT scan to acquire a tomographic image by X-rays (Step S3), and further, is subjected to PET scan to acquire a tomographic image by γ-rays (Step S4). An image (PET absorption correction image) of γ-ray absorption distribution in the object is generated based on data obtained by the X-ray CT scan (Step S3) (Step S5). Then, a PET/CT image after absorption correction is obtained based on the data obtained in the PET scan (Step S4) and the PET absorption correction image generated in Step S5 (Step S6).

In addition, the PET/CT apparatus 100 can operate not only as a normal PET apparatus but also as a TOF-PET apparatus in the PET scan (Step S4). Further, the absorption correction may be performed simultaneously with the data collection in the PET scan (Step S4).

The high-energy ray detector of the present embodiment uses the MCP of the electron multiplier for both the blocking of the high-energy ray and the multiplication of electrons, and thus, for example, can perform high speed detection at 50 ps or less. The high-energy ray detector of the present embodiment has the configuration in which the plurality of electron multipliers and the electron collector are stacked, and thus, the detection efficiency is high. Further, the detection efficiency can be further improved by providing the configuration in which the detection units are further stacked. When the plurality of detection units are stacked, potentials of electrodes of the opposing MCPs can be made equal, and thus, the number of wirings can be reduced. Further, there is no concern about a withstand voltage between the electrodes of the opposing MCPs, the interval therebetween can be reduced, and the high-energy ray detector can be made thin even when stacked.

In the above configuration, it is possible to minimize deterioration in detection efficiency due to the electron collector by forming the electron collector thin. Since the Cherenkov radiator and the scintillator are not required in the above configuration, the high-energy ray detector can be configured at low cost. Further, since the photoelectric conversion unit is not required, the high-energy ray detector can be easily configured at low cost. In the above configuration, there is no need for vacuum sealing when a vacuum space can be realized by the vacuum container.

It is possible to easily achieve multi-pixel configuration by arranging the plurality of conductive portions in the electron collector, and further, high spatial resolution can be realized since the electron multiplication by MCP is performed. The high-energy ray detector of the present embodiment can reduce the loss of spatial resolution and crosstalk caused by light as compared with a case in which a Cherenkov radiator or a scintillator and a photodetector are combined. Further, a spatial resolution of several tens of micrometers can be obtained by using the signal readout element in which the plurality of conductive portions are arranged one-dimensionally or two-dimensionally on the principal surface of the semiconductor substrate or using the signal readout element 50 as the electron collector.

When the high-energy ray detectors are arranged obliquely to radial lines passing through the center of a gantry in the PET apparatus, DOT measurement can be realized while eliminating an insensitive region. When a material of a base material of an MCP contains a large amount of lead which interacts strongly with the X-ray or γ-ray, the detection efficiency of the X-ray or γ-ray can be improved. Further, when the material of the base material of the MCP contains a material (B, Li, Gd, or the like) which interacts strongly with the neutron, the detection efficiency of the neutron can be improved.

The high-energy ray detector and the tomographic image acquisition apparatus are not limited to the above embodiments and configuration examples, and various modifications can be made.

The high-energy ray detector according to the above embodiment is configured to include (1) a first electron multiplier including one or more micro-channel plates each being configured to emit electrons by interaction with an incident high-energy ray, and multiply and output the electrons; (2) a second electron multiplier including one or more micro-channel plates each being configured to emit electrons by interaction with an incident high-energy ray, and multiply and output the electrons; and (3) an electron collector configured to be transmissive for the high-energy ray, collect the electrons multiplied and output from each of the first electron multiplier and the second electron multiplier, and output an electric pulse signal, and the first electron multiplier, the electron collector, and the second electron multiplier are arranged in this order along a predetermined direction.

In this case, the high-energy ray detector may be configured such that a plurality of detection units are arranged along the predetermined direction, and each of the plurality of detection units is constituted by the first electron multiplier, the electron collector, and the second electron multiplier, being arranged in this order along the predetermined direction.

The high-energy ray detector according to the above embodiment is configured to include a plurality of detection units arranged along a predetermined direction, and each of the plurality of detection units is constituted by an electron multiplier including one or more micro-channel plates each being configured to emit electrons by interaction with an incident high-energy ray, and multiply and output the electrons, and an electron collector configured to be transmissive for the high-energy ray, collect the electrons multiplied and output from the electron multiplier, and output an electric pulse signal, being arranged along the predetermined direction.

In addition, the high-energy ray detected by the high-energy ray detector of the above configuration is a γ-ray, an X-ray (in particular a hard X-ray), or a neutron ray.

In the above high-energy ray detector, the electron collector may be configured to include an insulating substrate, and a conductive portion provided on a principal surface of the insulating substrate. Further, in this case, the electron collector may be configured to include a plurality of conductive portions provided on the principal surface of the insulating substrate as the conductive portion, collect the electrons in each of the plurality of conductive portions, and output the electric pulse signal.

In the above high-energy ray detector, the electron collector may be configured to include a semiconductor substrate, and a plurality of conductive portions provided on a principal surface of the semiconductor substrate, and a circuit configured to read out the electric pulse signal output from each of the plurality of conductive portions may be formed on the semiconductor substrate.

In the above high-energy ray detector, a base material of the micro-channel plate may contain a material with a high atomic number, or a material which emits electrons by interaction with a neutron.

The tomographic image acquisition apparatus according to the above embodiment is an apparatus configured to acquire a tomographic image of an object placed in a measurement space, and is configured to include the high-energy ray detector of the above configuration as each of a plurality of detectors provided around the measurement space to detect the high-energy ray.

The above tomographic image acquisition apparatus may further include an X-ray source, and may be configured such that the high-energy ray detector is configured to detect an X-ray output from the X-ray source and transmitted through the object, and detect a γ-ray generated along with electron-positron annihilation in the object into which an RI source is introduced.

The present invention can be used as a thin high-energy ray detector that can be easily manufactured.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A high-energy ray detector comprising:
   a first electron multiplier including one or more micro-channel plates each configured to emit electrons by interaction with an incident high-energy ray, and multiply and output the electrons;
   a second electron multiplier including one or more micro-channel plates each configured to emit electrons by interaction with an incident high-energy ray, and multiply and output the electrons; and
   an electron collector configured to be transmissive for the high-energy ray, collect the electrons multiplied and output from each of the first electron multiplier and the second electron multiplier, and output an electric pulse signal, wherein
   the first electron multiplier, the electron collector, and the second electron multiplier are arranged in this order along a predetermined direction.

2. The high-energy ray detector according to claim 1, wherein
   a plurality of detection units are arranged along the predetermined direction, and
   each detection unit is constituted by the first electron multiplier, the electron collector, and the second electron multiplier, being arranged in this order along the predetermined direction.

3. The high-energy ray detector according to claim 1, wherein the electron collector includes an insulating substrate, and a conductive portion provided on a principal surface of the insulating substrate.

4. The high-energy ray detector according to claim 3, wherein the electron collector includes a plurality of conductive portions provided on the principal surface of the insulating substrate as the conductive portion, collects the electrons in each of the plurality of conductive portions, and outputs the electric pulse signal.

5. The high-energy ray detector according to claim 1, wherein the electron collector includes a semiconductor substrate, and a plurality of conductive portions provided on a principal surface of the semiconductor substrate, and a circuit configured to read out the electric pulse signal output from each of the plurality of conductive portions is formed on the semiconductor substrate.

6. The high-energy ray detector according to claim 1, wherein a base material of the micro-channel plate contains a material which emits electrons by interaction with a neutron.

7. A tomographic image acquisition apparatus configured to acquire a tomographic image of an object placed in a measurement space, the apparatus comprising:
   the high-energy ray detector according to claim 1 as each of a plurality of detectors provided around the measurement space to detect the high-energy ray.

8. The tomographic image acquisition apparatus according to claim 7, further comprising an X-ray source, wherein
   the high-energy ray detector is configured to detect an X-ray output from the X-ray source and transmitted through the object, and detect a γ-ray generated with electron-positron annihilation in the object into which an RI source is introduced.

* * * * *